(12) United States Patent
Orlu et al.

(10) Patent No.: US 7,654,984 B2
(45) Date of Patent: Feb. 2, 2010

(54) BODILY FLUID SAMPLING OR TRANSFUSION DEVICE WITH PROTECTION MEANS

(75) Inventors: Alain Orlu, Viuz la Chiesaz (FR); Pierre-André Commaret, Bogis-Bossey (CH)

(73) Assignee: P2A Medical, Albens (FR)

( * ) Notice: Subject to any disclaimer, the term of this patent is extended or adjusted under 35 U.S.C. 154(b) by 729 days.

(21) Appl. No.: 11/462,916

(22) Filed: Aug. 7, 2006

(65) Prior Publication Data
US 2007/0083165 A1    Apr. 12, 2007

(30) Foreign Application Priority Data
Aug. 8, 2005    (FR) .................................... 05 08501

(51) Int. Cl.
*A61M 5/178* (2006.01)
(52) U.S. Cl. .................. 604/164.08; 604/192; 604/197; 604/198
(58) Field of Classification Search ............... 604/192, 604/197–198, 164.08
See application file for complete search history.

(56) References Cited

U.S. PATENT DOCUMENTS

| 4,900,310 | A | 2/1990 | Ogle |
| 5,024,616 | A | 6/1991 | Ogle |
| 2003/0004437 | A1 | 1/2003 | Collins |
| 2005/0277893 | A1 | 12/2005 | Liversidge |

*Primary Examiner*—Kevin C Sirmons
*Assistant Examiner*—Deanna K Hall
(74) *Attorney, Agent, or Firm*—William H. Eilberg

(57) ABSTRACT

Sampling or transfusion device with protection means including a protective tube that slides longitudinally along the axis in an annular passage between the external body and the central body and has a proximal holding end for moving it selectively between a proximal retracted position in which the needle is not covered by the protective tube or not much covered thereby so that the latter can be used to draw a sample or to administer a transfusion and a distal protection position in which the protective tube covers the needle over the whole of its length.

18 Claims, 10 Drawing Sheets

BODILY FLUID SAMPLING OR TRANSFUSION DEVICE WITH PROTECTION MEANS

TECHNICAL FIELD OF THE INVENTION

The present invention relates to devices for drawing samples of bodily fluids or transfusion devices used in the medical world, and more particularly devices for drawing samples of bodily fluids or transfusion devices including protection means.

The devices for drawing samples of bodily fluid or transfusion devices routinely used in the medical world generally include a needle adapted to penetrate the body of a patient, for example a vein. Once the bodily fluid sample has been drawn or the transfusion has been administered, the needle is removed from the body of the patient, and is generally found to be carrying blood or other bodily fluids of the patient. If the patient is suffering from an infectious disease, that blood or other bodily fluids could be a source of contamination. But infections that the patient may be carrying are not always detected or detectable.

It is therefore necessary to provide systematic and effective protection of medical personnel against injuries that could be caused by needles contaminated with blood or other bodily fluids. It is also necessary to prevent blood or other bodily fluids from contaminating the environment, for example fixtures and fittings or other medical instruments.

To this end there are already known in the art blind tubular caps that are fitted around the needle of the bodily fluid sampling device or the transfusion device after drawing the sample or administering the transfusion.

These blind tubular caps have an interior housing adapted to contain the projecting portion of the needle. The diameter of the interior housing is only very slightly greater than the diameter of the needle. As a general rule these blind tubular caps also have very thin lateral walls.

This small inside diameter and this thin lateral wall oblige medical personnel to use both hands to insert the needle into its blind tubular protective cap, a first hand holding the cap and a second hand holding the needle. Inserting the needle into a housing whose diameter is only very slightly greater than its own diameter requires great dexterity, and also great care, because if the person should miss the internal housing of the blind tubular cap with the needle, there is a high risk of it pricking a finger of the first hand holding the cap, because of the thin lateral wall of the blind tubular cap.

Thus using the generally known blind tubular caps proves difficult for medical personnel and is not free of the risk of accidents that can lead to sometimes serious illnesses through contamination with blood or other bodily fluids carried by the needle.

Despite the risk, and because of these difficulties in using blind tubular caps to protect the needles of bodily fluid sampling devices or transfusion devices, medical personnel usually and intentionally fail to use them. In practice, they hold the sampling or transfusion device fitted with its needle (which is unprotected and contaminated with blood) in their hand, in the open air, or place the sampling or transfusion device complete with its needle soiled with the blood of the patient on a table or in a container containing other medical instruments. There is therefore a high risk of medical personnel injuring themselves with the needle soiled with the blood of the patient or injuring a person present in the room in which they are working. There is also a high risk of contaminating medical instruments and the working environment in general.

There is further a high risk of medical personnel being splashed with blood on a needle that has just been withdrawn from the body of a patient.

The document WO 2004/000397 describes a bodily fluid sampling device or a transfusion device with an automatic protection system. In that document, a tube covers the projecting portion of a needle and slides to uncover it as the needle penetrates the body of a patient. The tube then covers the projecting portion of the needle again as the latter is withdrawn from the body of the patient. A system of this kind is not easy to handle and inaccurate when injecting a patient, and can therefore cause clumsy manipulation by hospital personnel, causing unnecessary suffering to the patient. The system also comprises many components, including a spring, and it is complex and time-consuming to assemble.

The document EP 0 363 180 describes a bodily fluid sampling device or a transfusion device with protection means, including:
  a central longitudinal hollow body that enables a fluid to pass between a first end and a second end, is provided at its proximal end with means for connecting it to a transfusion or sampling line, and is attached to a coaxial needle that projects from its distal end,
  an external longitudinal hollow body that is attached to the central body, disposed concentrically around the central body and conformed to constitute holding means for a user to hold,
  an annular passage between the central body and the external body,
  a protective tube with a discontinuous longitudinal slot that is mounted to slide longitudinally in the annular passage between the external body and the central body and is provided with a proximal holding end adapted to be moved selectively between a proximal retracted position in which the needle is not covered or not much covered by the protective tube and a distal protection position in which the protective tube covers the entire length of the needle.

In the above document, the central body is necessarily separate from the external body and must be attached to the external body by a small pin that is force-fitted or adhesively bonded into transverse holes in the central body and the external body and that runs freely through a discontinuous longitudinal slot in the protective tube. Because of the large number of components to be manufactured and then assembled, and because this kind of assembly operation is difficult and time-consuming, the unit cost is too high for a disposable device.

The document EP 0 369 619 describes a device inspired by the device of the document EP 0 363 180 that has the same drawbacks in respect of assembling it.

SUMMARY OF THE INVENTION

A first problem addressed by the invention is to design a low cost protection system that is reliable and easy for medical personnel to manipulate with one hand.

The invention aims more particularly to design a sampling or transfusion device of this kind that is simple and inexpensive to manufacture and assemble.

Another aspect of the invention aims to provide a sampling or transfusion device incorporating protection means that can be used with no risk of contaminating either medical personnel or the working environment, avoid manipulation of the protection means by the hand of the user in the vicinity of the dangerous end of the needle, and avoid any movement toward the dangerous end of the needle.

The invention simultaneously aims to eliminate all risk of the user mislaying the protection means.

The invention simultaneously aims to design a device that does not oblige medical personnel to perform complicated or unusual gestures to use it.

The invention further aims to design a sampling or transfusion device incorporating protection means that is practical and hygienic and allows only one use of the sampling or transfusion device.

To achieve the above and other objects, the invention proposes a bodily fluid sampling or transfusion device incorporating protection means, said device including:
- a longitudinal hollow central body that enables a fluid to flow between a first end and a second end, is provided at its proximal end with means for connecting it to a sampling or transfusion line and is attached to a coaxial needle that projects from its distal end,
- means for selectively covering the projecting portion of the needle after use,
- a longitudinal hollow external body that has a peripheral tubular wall, is attached to the central body, is disposed concentrically around the central body and is conformed to constitute holding means for a user to hold onto,
- an annular passage between the central body and the external body,
- a protective tube that can slide longitudinally in the annular passage between the external body and the central body and has a proximal holding end for moving it selectively between, on one hand a proximal retracted position in which the needle is not covered by the protective tube or only very slightly covered thereby so that it can be used to draw a sample or to administer a transfusion, and on the other hand a distal protection position in which the protective tube covers the needle over its entire length,
- at least one radial fixing bridge attaching the external body to the central body and extending radially from the central body to the external body, and
- at least one longitudinal slot that extends over at least a portion of the length of the protective tube and in which said at least one radial fixing bridge slides during sliding movement of the protective tube relative to the central body and the external body, in which device:
- the central body, the radial fixing bridge and the external body are in one piece, and
- the longitudinal slot extends as far as the distal end of the protective tube.

The above kind of system ensures effective protection of the needle and of users. Moreover, it is simple and quick to use, and requires the user to use only one hand. Manipulation of the protection means by the hand of the user in the vicinity of the dangerous end of the needle is avoided, and especially any movement toward the dangerous end of the needle, which could cause the user to prick his hand with the needle.

It is also impossible for the user to mislay the protection means, as they are attached to the sampling or transfusion device. The protection means are therefore always available.

The production of the central body, the radial fixing bridge and the external body in one piece is particularly beneficial from the economic point of view. It is no longer necessary to assemble multiple small components that can easily be mislaid, which helps to reduce considerably the assembly cost and therefore the production cost of the device.

The fact that the longitudinal slot in the protective tube extends as far as its distal end means that the protective tube can be fitted into the annular passage between the central body and the external body by means of a simple movement in translation, because the radial fixing bridge can enter the longitudinal slot of the protective tube at its open distal end. Fitting the protective tube is therefore very simple, fast and easy.

The proximal holding end of the protective tube can advantageously include at least one radial pusher tab extending radially away from the protective tube.

The sampling or transfusion device of the invention therefore includes holding means similar to those of a conventional syringe. This guarantees that medical personnel need to use only one hand to use the protection means of the invention, this involving an easy gesture that is commonplace in the medical profession, and therefore with no risk of incorrect manipulation.

The resulting holding means are furthermore easy to produce and of low cost.

The sampling or transfusion device of the invention with protection means may advantageously include means for locking the protective tube in the distal protection position and/or the proximal retracted position.

Locking the protective tube in the proximal retracted position enables use of the sampling or transfusion device with no risk of conflict between the protection means including the protective tube and the surrounding environment. For example, the protective tube will not slide unintentionally in the vicinity of the body of the patient when drawing a sample or administering a transfusion. This guarantees the quality of the injections effected by medical personnel.

Locking the protective tube in the distal protection position effectively prevents all risk of unintentional sliding of the protective tube that could expose the needle of the sampling or transfusion device again after it has been used and then covered over the whole of its length by the protective tube.

The proximal retracted position locking means may preferably include:
- a first annular peripheral notch on the protective tube in the vicinity of its distal end, and
- at least one elastic radial locking lug extending radially from a distal end of the external body and engaging in the first annular peripheral notch when the protective tube is in the proximal retracted position.

Similarly, the distal protection position locking means may advantageously include:
- a second annular peripheral notch or a shoulder with a face facing toward the proximal holding end on the protective tube in the vicinity of its proximal holding end, and
- at least one elastic radial locking lug extending radially from the distal end of the external body and accommodated in the second annular peripheral notch or located over the shoulder when the protective tube is in the distal protection position.

This provides proximal retracted position locking means and distal protection position locking means that are simple, practical, economical and most importantly compact, again so as not to encumber the working space of the medical personnel unnecessarily, as much for reasons of the quality of their work as for reasons of their safety. Holding and manipulating the sampling or transfusion device of the invention are also facilitated.

In a different embodiment of the invention, the proximal retracted position locking means may include:
- at least one first stop extending radially away from the protective tube in the vicinity of its distal end, and
- at least one longitudinal locking lug in an opening in the peripheral tubular wall of the external body that is adapted to be flexed elastically in the radial direction and has a free end oriented toward the proximal end of the external body adapted to abut against the first stop when the protective tube is in the proximal retracted position.

In this other embodiment, the distal protection position locking means may advantageously include:

at least one second stop extending radially away from the protective tube in the vicinity of its proximal end, and an opening in the locking lug adapted to receive the second stop when the protective tube is in the distal protection position.

These locking means are easy to manufacture, easy to remove from the mold, reliable and effective in locking the protective tube.

According to the invention, the sampling or transfusion device with protection means may include a removable blind tubular protective cap that is conformed to fit over the distal end of the external body around the projecting portion of the needle and is of sufficient diameter to receive the projecting distal portion of the protective tube in the distal protection position.

On one hand the cap may protect the needle before use.

On the other hand the presence of this removable blind tubular protective cap, fitted over the distal end of the external body that surrounds the projecting portion of the needle after use, ensures a perfect seal and collects any drops of blood that may drop off the needle when contaminated with the blood of a patient.

When fitted over the distal end of the external body, the blind tubular protective cap may preferably oppose elastic radial expansion of said at least one locking lug and thereby prevent unlocking and sliding of the protective tube.

According to the invention, the blind tubular protective cap may include at its closed end retaining means for retaining the protective tube in the distal protection position.

This avoids all risk of the blind tubular protective cap coming off once it has been fitted over the distal end of the external body after use.

The retaining means for retaining the protective tube may advantageously be conformed to engage in a first annular peripheral notch of the protective tube when the protective tube is in the distal protection position and the protective cap is fitted over the distal end of the external body.

This is a practical and economical way to retain the protective tube after use, guaranteeing single use of the device.

The central body, the external body and the protective cap may advantageously be made of plastic material, yielding a device that is low in weight and cheap to produce.

BRIEF DESCRIPTION OF THE DRAWINGS

Other objects, features and advantages of the present invention will emerge from the following description of particular embodiments of the invention given with reference to the appended drawings, in which.

DESCRIPTION OF THE PREFERRED EMBODIMENTS

Figure 1:
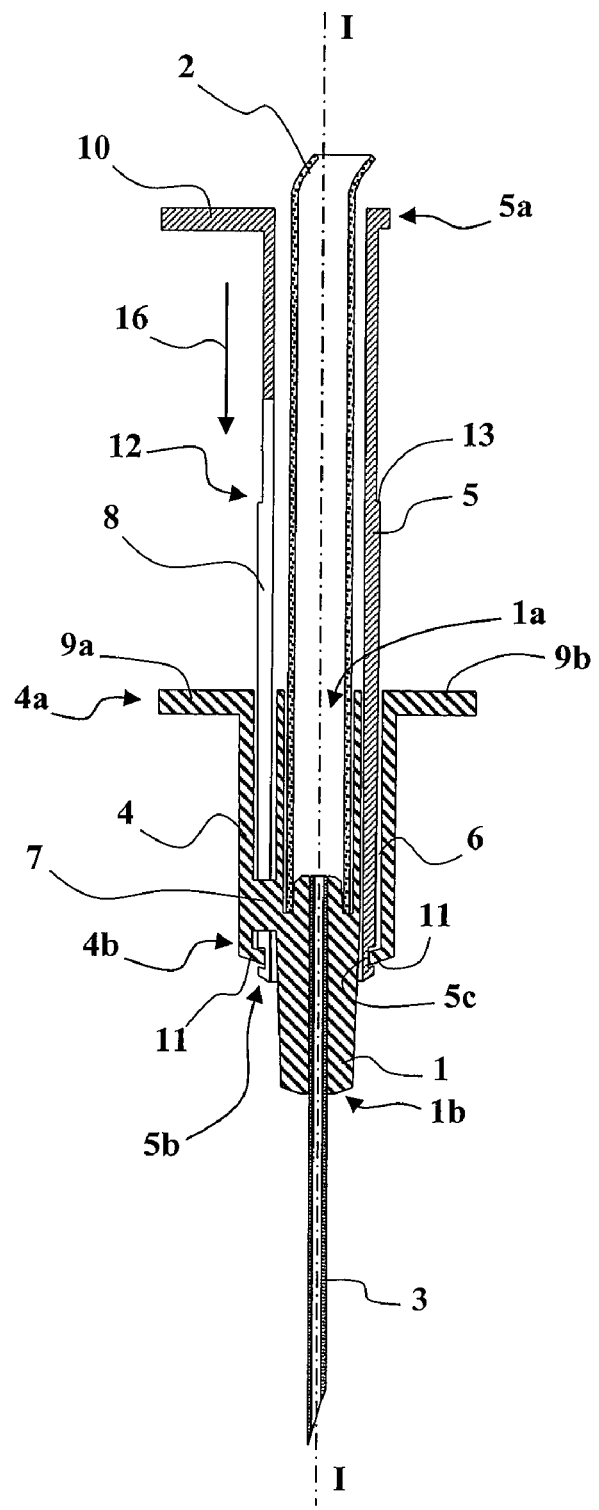
FIG. 1 is a view in longitudinal section of a first embodiment of a sampling or transfusion device with protection means, showing a protective tube in a proximal retracted position.
Figure 2:
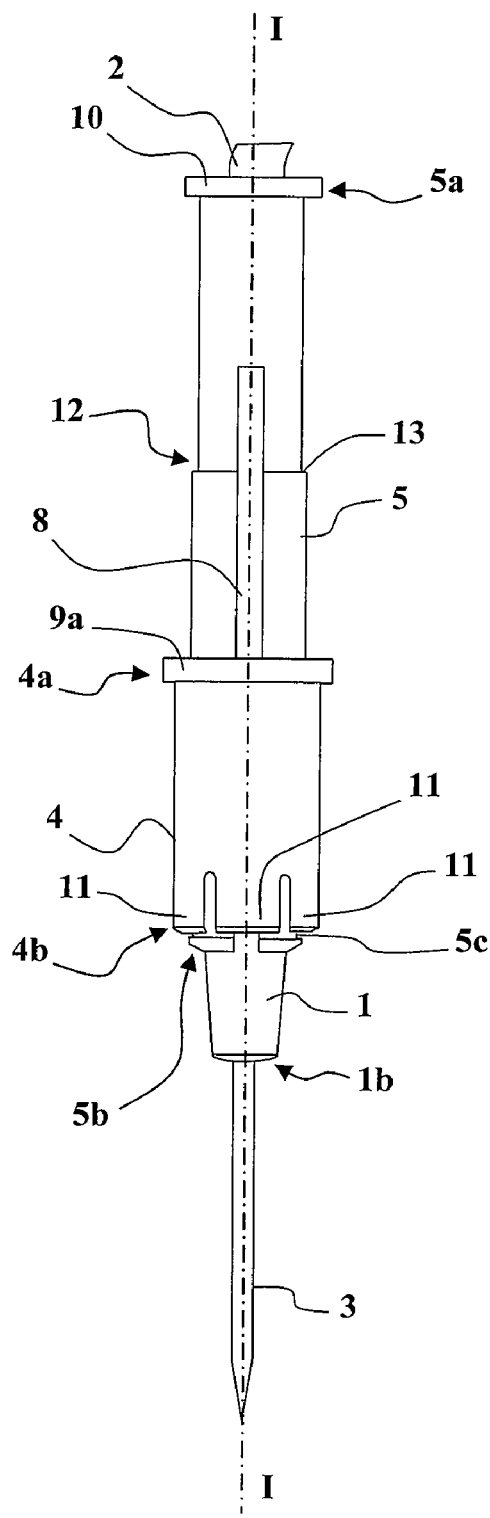
FIG. 2 is a side view of the sampling or transfusion device with protection means from FIG. 1 in a plane offset 90° relative to the plane of FIG. 1.

In the embodiments shown in FIGS. 1 to 11, a sampling or transfusion device according to the invention incorporating protection means includes a longitudinal hollow central body 1 through which a bodily fluid such as blood can pass between a first end and a second end and is provided at its proximal end 1a with means for connecting it to a sampling or transfusion line 2 and is attached to a coaxial needle 3 that projects from its distal end 1b. A longitudinal hollow external body 4 attached to the central body 1 is disposed concentrically around the central body 1 and is conformed to constitute holding means for a user to hold onto. A protective tube 5 selectively covers the projecting portion of the needle 3 after use, sliding longitudinally along the axis I-I in an annular passage 6 between the central body 1 and the external body 4.

The central body 1 is molded over the needle 3.

The protective tube 5 has a proximal holding end 5a that is selectively movable between a proximal retracted position (FIG. 1) in which the needle 3 is not covered by the protective tube 5, or not much covered thereby, so that it can be used for drawing a sample or administering a transfusion, and a distal protection position (FIGS. 3 and 4) in which the protective tube 5 covers the whole length of the needle 3.

Figure 5:
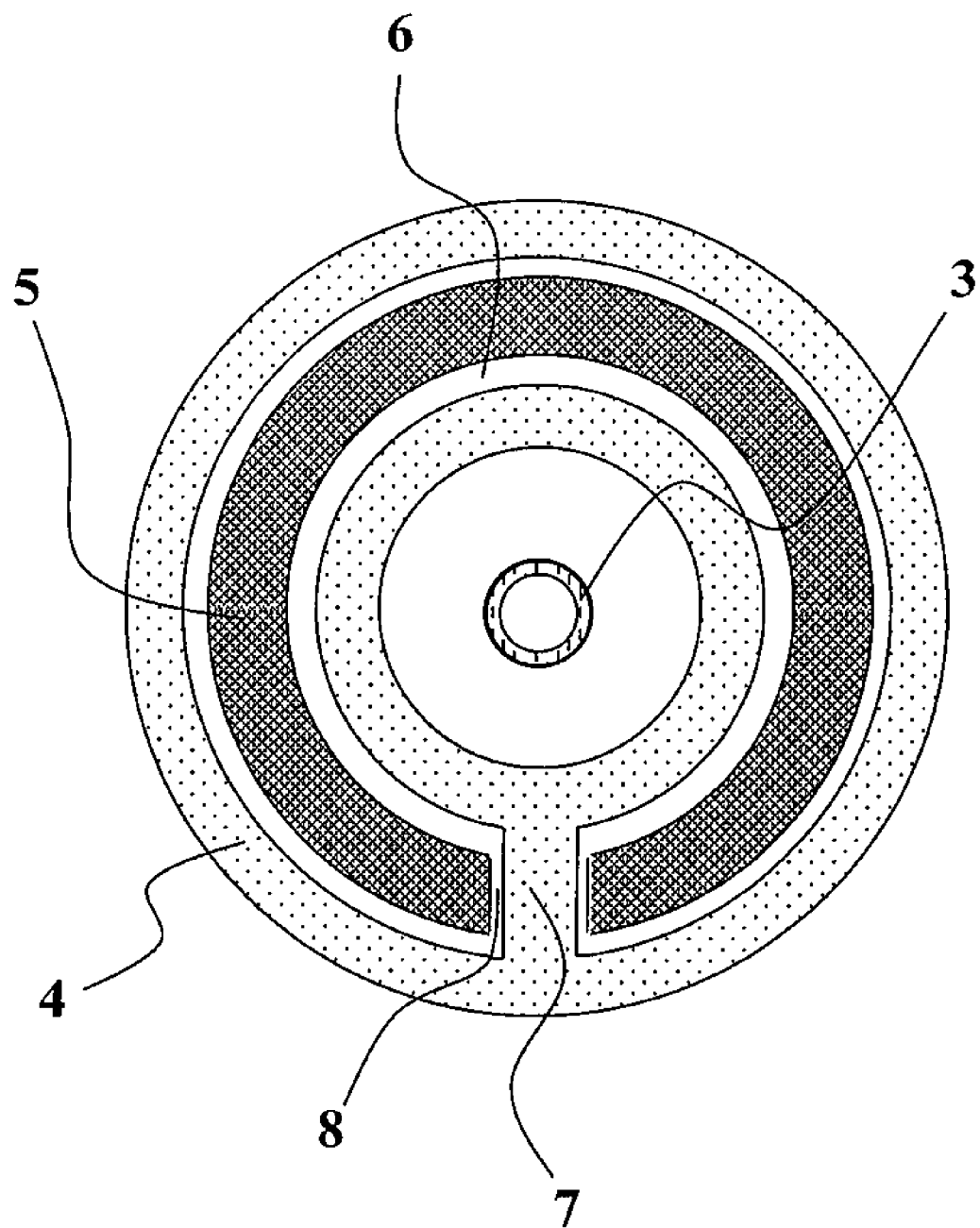
FIG. 5 is a view in cross section of the sampling or transfusion device with protection means from FIGS. 1 to 4.

FIGS. 1 and 5 in particular show that the external body 4 is attached to the central body 1 by a radial fixing bridge 7 extending radially from the central body 1 to the external body 4. The protective tube 5 slides longitudinally in the annular passage 6 between the central body 1 and the external body 4.

The central body 1, the radial fixing bridge 7 and the external body 4 are in one piece. The one-piece construction of the central body 1, the radial connecting bridge 7 and the external body 4 considerably reduces the time to manufacture and assemble the sampling or transfusion device and therefore reduces its cost.

For the protective tube 5 to be able to slide longitudinally along the axis I-I, it includes over at least a portion of its length at least one longitudinal slot 8 in which said radial fixing bridge 7 slides during longitudinal sliding movement of the protective tube 5 relative to the central body 1 and the external body 4. This longitudinal slot 8 is seen more clearly in FIG. 2.

The longitudinal slot 8 extends as far as the distal end 5b of the protective tube 5. This enables the protective tube 5 to be inserted into the annular passage 6 between the central body 1 and the external body 4 by a simple movement in translation along the axis I-I.

Figure 10:
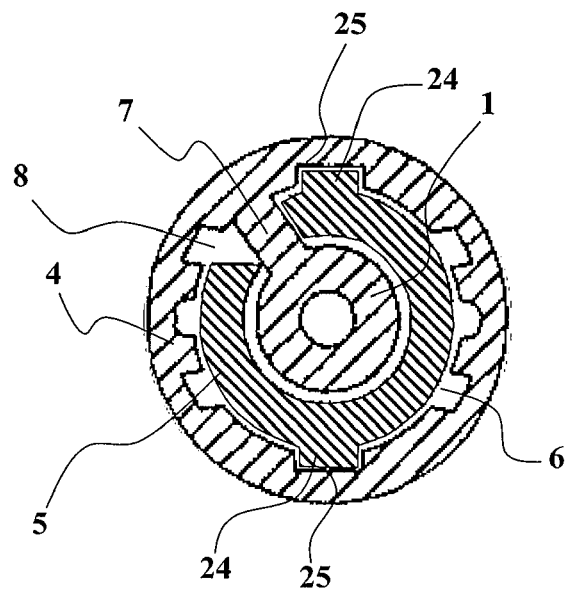
FIG. 10 is a view of the device in cross section along the plane A-A from FIG. 6, without the blind protective cap.

In the embodiment shown in FIGS. 1 to 11, the external body 4 is attached to the central body 1 by only one radial fixing bridge 7 (FIGS. 5 and 10). Obviously more than one radial bridge 7 can be used to fasten together the central body 1 and the external body 4.

The protective tube 5 being slotted over a major portion of its length, and the longitudinal slot 8 extending as far as the distal end 5b of the protective tube 5, the protective tube 5 may be lacking in stiffness. This lack of stiffness could compromise good axial sliding of the protective tube 5 in the annular passage 6 between the central body 1 and the external body 4 (FIGS. 5 and 10). To stiffen the protective tube 5 for improved guidance thereof as it slides along the axis I-I, in the second embodiment of the invention the protective tube 5 includes longitudinal ribs 24 (FIGS. 9 and 10) adapted to cooperate with longitudinal grooves 25 in the external body 4.

In the sampling or transfusion device according to the invention incorporating protection means shown in FIGS. 1 to 11, the external body 4 includes two radial holding tabs 9a and 9b extending radially away from the external body 4 in the vicinity of the proximal end 4a of the external body 4. The proximal holding end 5a of the protective tube 5 includes a radial pusher tab 10 extending radially away from the protective tube 5.

The handling means of the sampling or transfusion device with protection means are therefore similar to those of a standard syringe, and medical personnel using this device will therefore have no trouble in holding or using it. Syringes are routinely used in the medical world and the sampling or transfusion device of the invention incorporating protection means is advantageously held by an easy gesture that is frequently used by medical personnel. This avoids all handling risks linked to a complicated or unusual way of holding the device.

What is more, the user can hold the sampling or transfusion device of the invention incorporating protection means in one hand and move the protective tube 5 relative to the external body 4 and the central body 1 with that one hand remaining well away from the needle 3. This frees one hand of the user, who is usually obliged to perform several tasks at the same time to draw a sample or administer a transfusion. For example, the user may have to rub the sampling or transfusion site on the body of the patient with cotton wool. The user may also have to hold the cotton wool pressed onto the sampling or transfusion site on the body of the patient to prevent bleeding as soon as the sampling or transfusion device is withdrawn after drawing a sample or administering a transfusion. The patient cannot hold the cotton wool himself if he is unconscious, for example.

Figure 3:
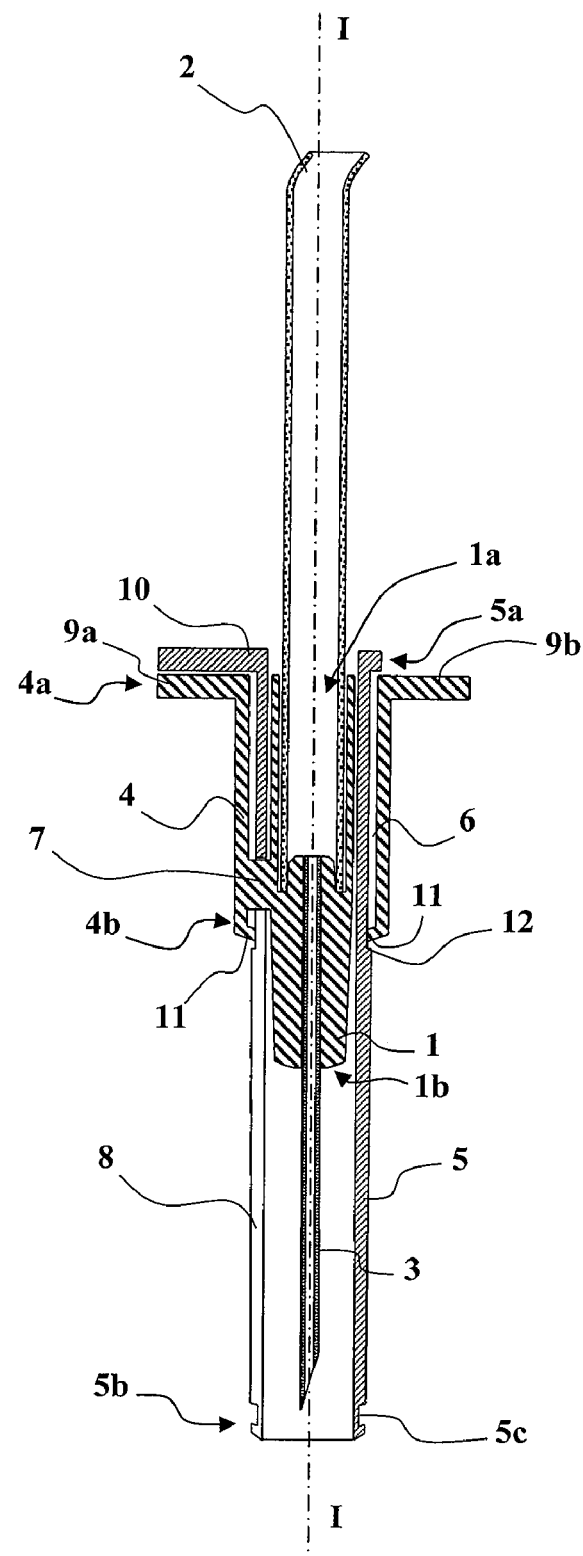
FIG. 3 is a view in longitudinal section of the sampling or transfusion device with protection means from FIGS. 1 and 2, showing the protective tube in a distal protection position.
Figure 4:
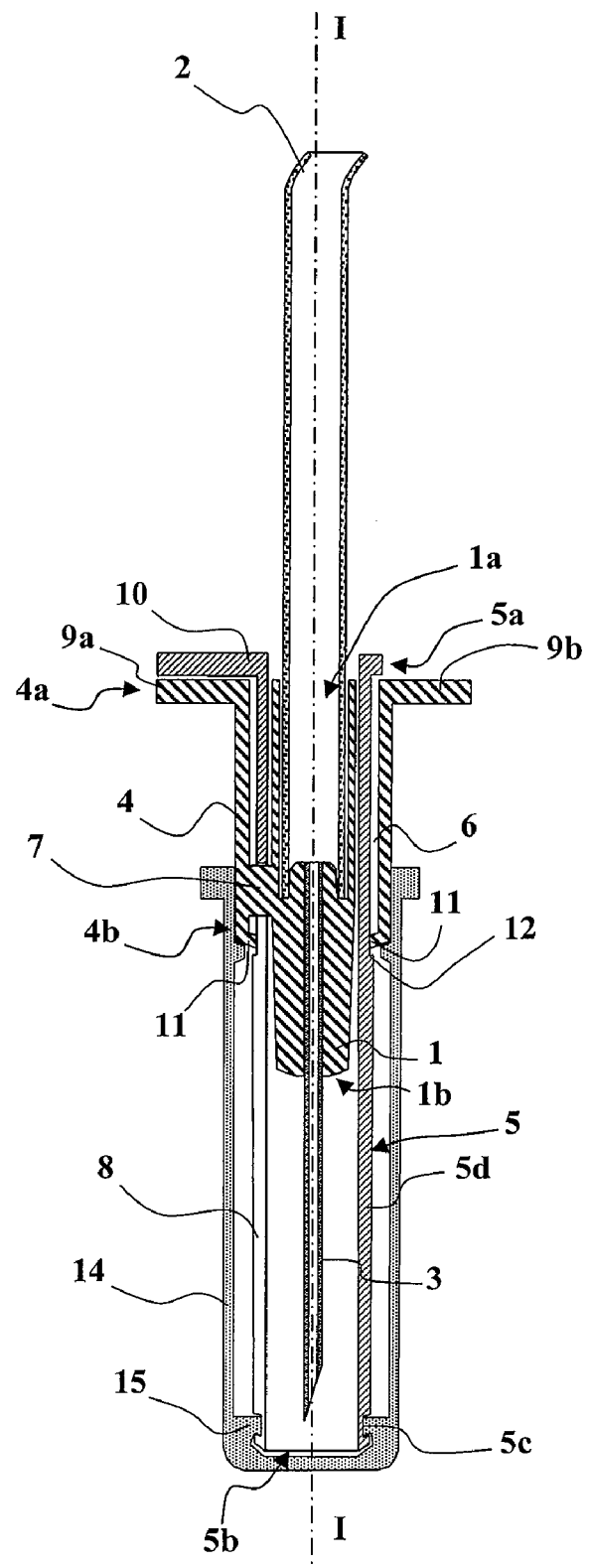
FIG. 4 is a view in longitudinal section of the sampling or transfusion device with protection means from FIGS. 1 to 3, showing the protective tube in the distal protection position and fitted with a blind tubular protective cap.

In FIGS. 1, 3 and 4 the first embodiment of the sampling or transfusion device of the invention incorporating protection means includes means for locking the protective tube 5 in the distal protection position and means for locking the protective tube 5 in the proximal retracted position.

The proximal retracted position locking means include:
a first annular peripheral notch 5c on the protective tube 5 in the vicinity of its distal end 5b, and
elastic radial locking lugs 11 extending radially from a distal end 4b of the external body 4 and accommodated in the first annular peripheral notch 5c when the protective tube 5 is in the proximal retracted position (FIG. 1).

The distal protection position locking means include:
a shoulder 12 with a radial face 13 facing toward the proximal holding end 5a of the protective tube, formed on the protective tube 5 in the vicinity of its proximal holding end 5a, and elastic radial locking lugs 11 extending radially from the distal end 4b of the external body 4 and locating over the shoulder 12 when the protective tube 5 is in the distal protection position (FIGS. 3 and 4).

FIGS. 6, 7, 8, 9 and 11 show the second embodiment of the invention with another type of locking means for locking the protective tube 5 in the distal protection position and in the proximal retracted position.

Figure 7:
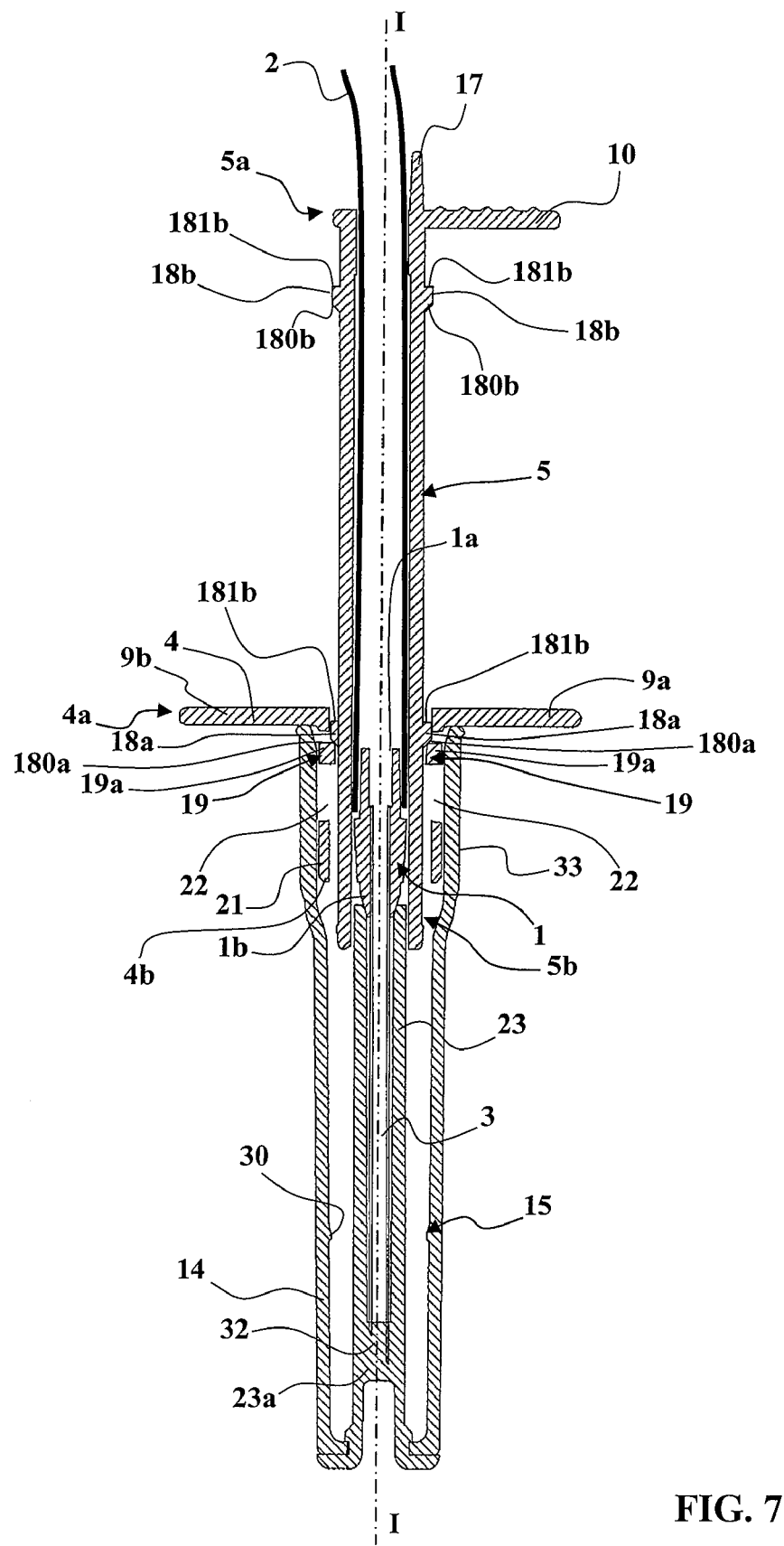
FIG. 7 is a front view of the FIG. 6 device in longitudinal section.
Figure 8:
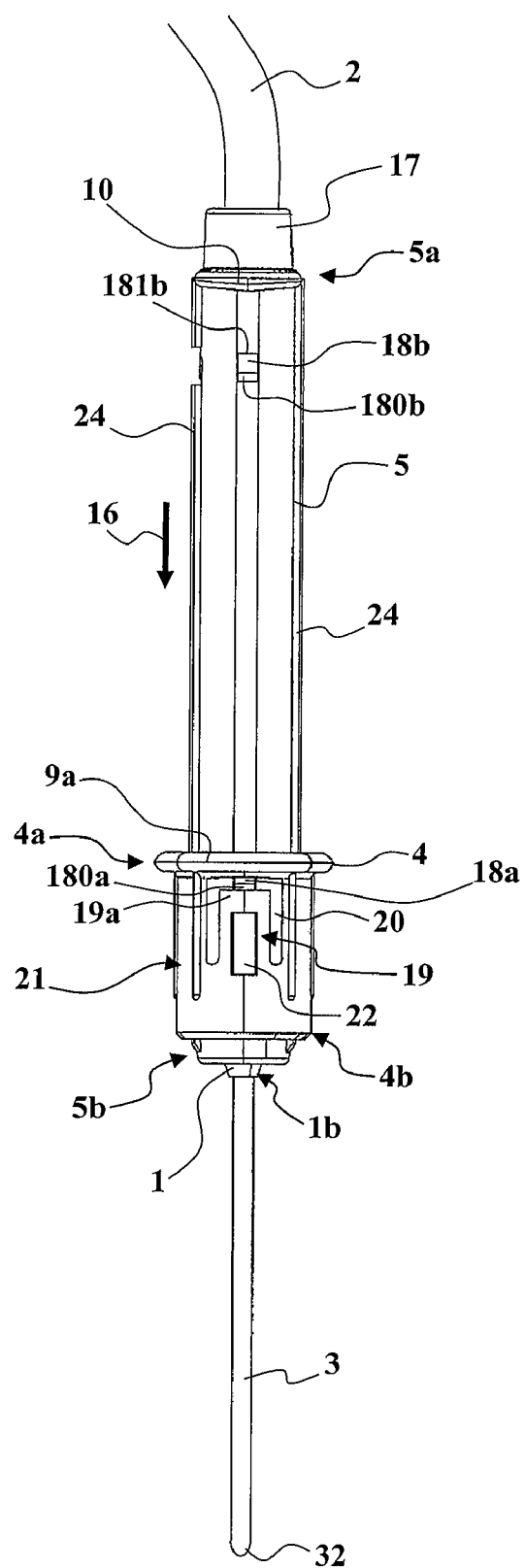
FIG. 8 is a side view of the FIG. 6 device in a plane offset 90° relative to the plane of FIG. 6, showing a protective tube in the proximal retracted position.
Figure 9:
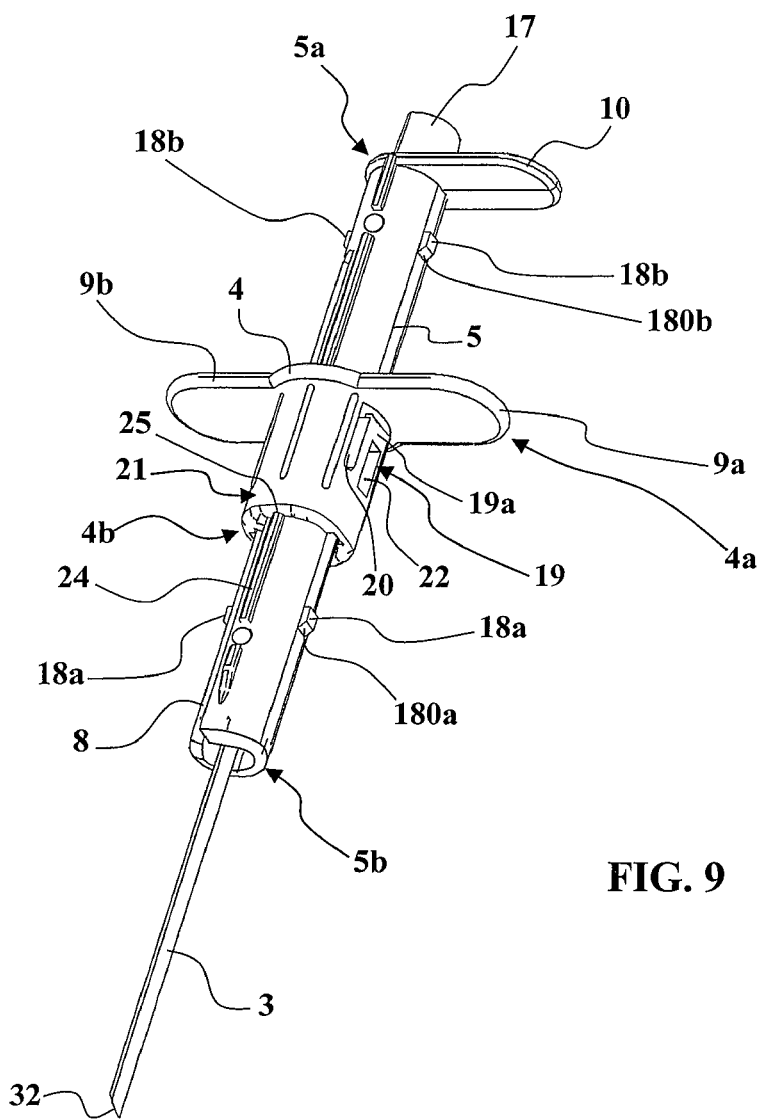
FIG. 9 is a perspective view of the device from FIGS. 6 to 8.

The proximal retracted position locking means include:
two first stops 18a extending radially away from the protective tube 5 in the vicinity of its distal end 5b, and
two longitudinal locking lugs 19 in two openings 20 (FIG. 8) in the peripheral tubular wall 21 of the external body 4 adapted to be deflected elastically in the radial direction and having a free end 19a oriented toward the proximal end 4a of the external body 4 adapted to abut against the first stop 18a when the protective tube 5 is in the proximal retracted position (FIGS. 7 and 8).

Figure 11:
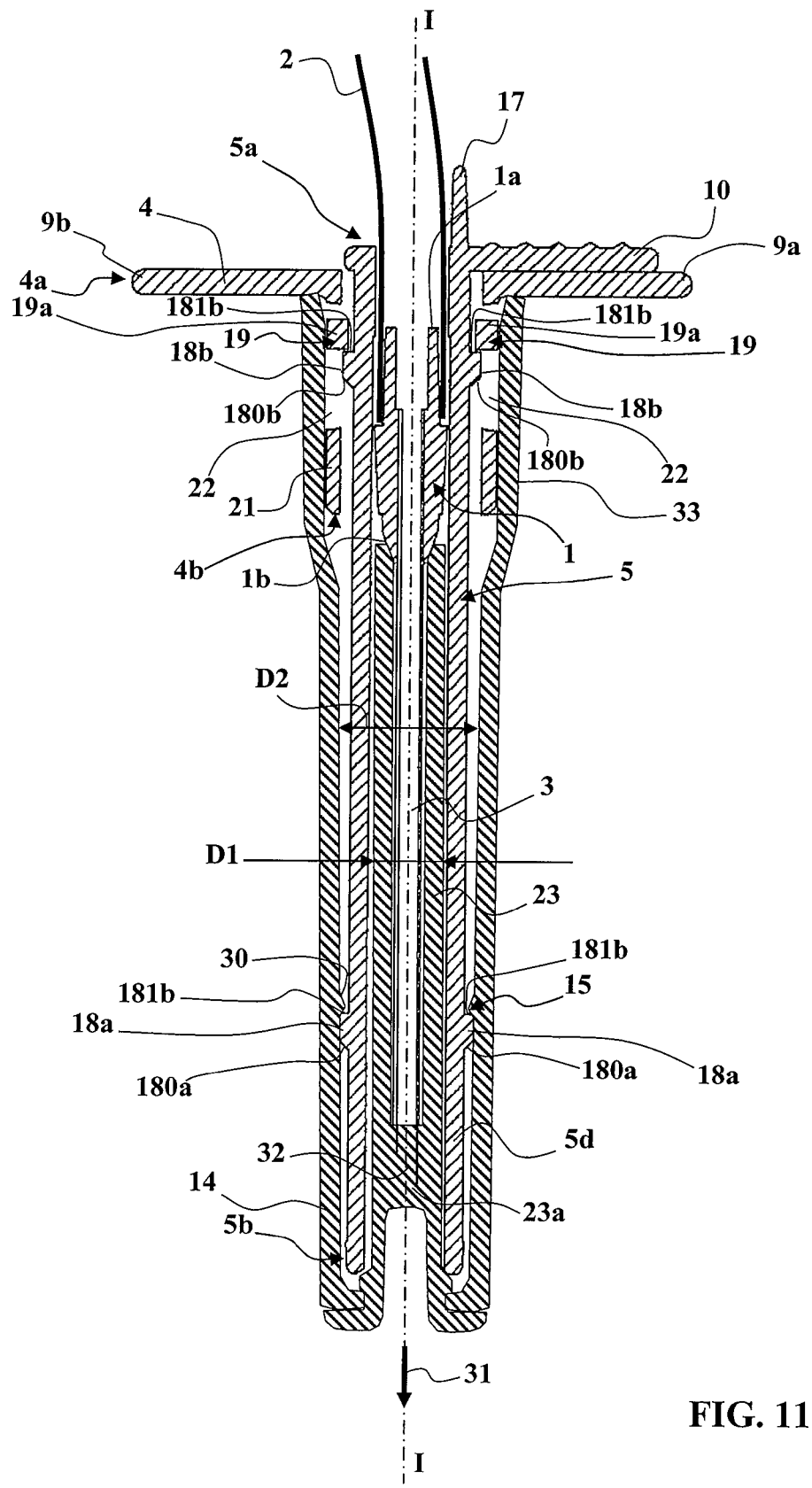
FIG. 11 is a view in longitudinal section of the device from FIGS. 6 to 10, showing a protective tube in the distal protection position.

The distal protection position locking means include:
two second stops 18b extending radially away from the protective tube 5 in the vicinity of its proximal end 5a, and
openings 22 in the locking lugs 19 adapted to receive the second stops 18b when the protective tube 5 is in the distal protection position (FIG. 11).

Proximal retracted position and distal protection position locking means of the above kind are easily produced by injection molding a plastic material. The locking lugs 19 and the openings 20 and 22 may be produced by transverse mold cores when injection molding a plastic material.

The proximal retracted position locking means prevent unintentional sliding of the tube when the needle 3 is inserted into the body of a patient. Unwanted sliding of the protective tube 5 could then come into conflict with the body of the patient and could be a source of discomfort for the patient when drawing a sample or administering a transfusion.

The distal protection position locking means also and effectively prevent all risk of unwanted sliding of the protective tube 5 that could uncover the needle 3 when the protective tube 5 has been placed in the distal protection position after use. This prevents any subsequent contact with the needle 3 soiled by the blood of the patient, even accidental contact therewith.

In the medical environment in which samples are drawn and transfusions administered, to prevent all risk of cross-contamination between patients, it is particularly important to ensure that equipment that has been used once is never used again for another patient. It is therefore particularly beneficial to have a disposable sampling or transfusion device, and for this reason the sampling or transfusion device of the invention incorporating protection means advantageously prevents any attempt at subsequent reuse of the device once the protective tube 5 has been moved to the distal protection position after a first use of the device.

To this end, the elastic radial rocking lugs 11 of the first embodiment of the invention shown in FIGS. 1, 3 and 4 extend obliquely to the longitudinal axis I-I. This allows unidirectional sliding of the protective tube 5 from its proximal retracted position toward its distal protection position and prevents the protective tube 5 sliding from its distal protection position toward its proximal retracted position.

FIGS. 7 and 11 show that in the second embodiment of the invention the first and second stops 18a and 18b have distal oblique faces 180a and 180b that can deflect the locking lugs 19 laterally and elastically when the protective tube 5 slides longitudinally along the axis I-I.

The first and second stops 18*a* and 18*b* further each include a proximal shoulder 181*a* and 181*b* facing toward the proximal end 5*a* of the protective tube 5. The shoulders 181*a* and 181*b* allow only unidirectional sliding of the protective tube 5 from its proximal retracted position toward its distal protection position.

The shoulder 181*b* prevents the protective tube 5 from sliding from its distal protection position (FIG. 11) toward its proximal retracted position (FIG. 7). This guarantees that the sampling or transfusion device of the invention can be used only once.

When the protective tube 5 is in the distal protection position, all risk of medical personnel being injured by the needle 3 contaminated by the blood of the patient and all risk of re-use are eliminated.

Although most drops of blood that may drop off the needle 3 when soiled by the blood of a patient are collected by the protective tube 5, it may nevertheless happen that a few drops escape from the protective tube 5 through its longitudinal slot 8 or its open distal end 5*b*. Nor is there anything to prevent a child injuring itself with a sampling or transfusion device of the invention of this kind, even when the protective tube 5 is in the distal protection position, by inserting a small finger into the open distal end 5*b* of the protective tube 5. The inserted finger could then come into contact with the needle 3 after it has been soiled by the blood of a patient.

To provide this seal, and to avoid all risk of a child injuring itself, the sampling or transfusion device of the invention incorporating protection means may advantageously include a removable blind tubular protective cap 14 shaped to fit over the distal end 4*b* of the external body 4, around the projecting portion of the needle 3, and of sufficient diameter to receive the projecting distal section 5*d* of the protective tube 5 in the distal protection position (FIGS. 4 and 11).

In the second embodiment that is shown in FIG. 7, the protective cap 14 is fitted onto the external body 4 with the free ends 19*a* of the locking lugs 19 abutted against the oblique distal faces 180*a* of the first stops 18*a*. Because of the presence of the protective cap 14, the locking lugs 19 cannot deflect elastically in the radial direction. This prevents axial sliding of the protective tube 5 before the sampling or transfusion device is used, as its use starts with the removal of the protective cap 14 from the external body 4.

After use, and after fitting the protective cap 14 over the distal end 4*b* of the external body 4 (FIGS. 4 and 11), the blind tubular protective cap 14 opposes radial elastic expansion of the locking lugs 11 or 19 and thereby helps to prevent the protective tube from sliding from its distal protection position toward its proximal retracted position.

To increase safety even further, it is desirable for the protective cap 14 to be difficult if not impossible to remove once it has been fitted over the distal end 4*b* of the external body 4.

To this end, the blind tubular protective cap 14 includes means 15 for retaining the protective tube 5 in the distal protection position.

In FIG. 4, the retaining means 15 for the protective tube 5 are in the closed end of the cap and are conformed to engage in the first annular peripheral notch 5*c* in the protective tube 5 when the protective tube 5 is in the distal protection position and the protective cap 14 is fitted over the distal end 4*b* of the external body 4.

The retaining means 15 for the protective cap 14 may also be conformed in a similar way to the locking lugs 11, to ensure unidirectional movement of the protective cap 14 relative to the protective tube 5 and to prevent removal of the protective cap 14 once the latter has been fitted over the distal end 4*b* of the external body 4. This guarantees that the sampling or transfusion device can be used only once to draw a sample or to administer a transfusion.

In FIG. 11, the retaining means 15 for the protective tube 5 include an annular boss 30 inside the protective cap 14. The annular boss 30 cooperates with the first stops 18*a* to prevent the protective cap 14, once fitted over the distal end 4*b* of the external body 4, from being withdrawn in the direction defined by the arrow 31 when the protective tube 5 is in the distal protection position.

When a sampling or transfusion device with protection means according to the invention is used, the user (for example a nurse) removes the protective cap 14, if necessary, and then inserts the needle 3 into the body of the patient, the protective tube 5 being and remaining in the proximal retracted position (FIGS. 1 and 8). The transfusion or sampling line 2 is then connected to a sampling tube or to a transfusion sachet.

Once the transfusion has been administered or the sample drawn, the user holds the proximal end 4*a* of the external body 4 of the sampling or transfusion device in one hand, with one finger under the radial holding tab 9*b* and another finger under the radial holding tab 9*a*. The user then withdraws the needle 3 soiled by the blood of the patient from the body of the patient. To avoid all risk of contamination or injury by the needle 3 soiled by the blood of the patient, the user then immediately presses axially on the radial pusher tab 10 with the thumb of the same hand to move the protective tube 5 axially from its proximal retracted position (FIGS. 1 and 8) to its distal protection position (FIGS. 3 and 11), this movement being illustrated by the arrow 16. Thus the user manipulates the protective tube 5 away from the dangerous end of the needle 3 and by a movement that cannot come up against the dangerous end of the needle 3. The needle 3 is protected at this stage and there is no longer any risk of injury or contamination by the needle 3 soiled with the blood of the patient. The user has to use only one hand to withdraw the sampling or transfusion device according to the invention and to protect immediately the needle 3 soiled by the blood of the patient. For that purpose the user performs a standard movement that is well known to the user, because it is used to manipulate standard syringes, which ensures that there is no risk of mishandling the sampling or transfusion device according to the invention incorporating protection means.

In the second embodiment of the invention, the proximal holding end 5*a* of the protective tube 5 includes a protuberance 17 extending along part of the protective tube 5, in the longitudinal direction and beyond the radial pusher tab 10. The protuberance 17 extends from at least the portion of the circumference of the protective tube 5 from which the radial pusher tab 10 in particular extends. When the user presses axially on the radial pusher tab 10 with his thumb, the protuberance 17 prevents the user's thumb from crushing or bending the transfusion or sampling line 2 (FIG. 11). This effectively prevents impeding the flow of fluid between the needle 3 and the sampling tube or the transfusion sachet connected to the transfusion or sampling line 2.

While withdrawing the sampling or transfusion means incorporating protection means and protecting the needle 3 soiled with the blood of the patient by means of the protective tube 5, the user can, with his other hand, perform another task, such as holding a piece of cotton wool pressed against the transfusion or sampling site on the body of the patient.

Once in the distal protection position, the protective tube 5 is locked by the locking lugs 11 (FIG. 3) or 19 (FIG. 11) and can no longer slide from its distal protection position toward its proximal retracted position. Thus sampling or transfusion devices that have been used once may readily be identified visually by users, and even if users were to attempt to use them again, the locking lugs 11 or 19 preventing sliding of the protective tube 5 would make this impossible.

To ensure a perfect seal and total safety of the device of the invention, the user may fit the protective cap 14 over the distal end 4b of the external body 4. The latter is locked by the retaining means 15 engaged in the first annular peripheral notch 5c of the protective tube 5 (FIG. 4) or by cooperation of the annular boss 30 with the first stops 18a (FIG. 11). It is therefore impossible to remove the protective cap 14 once it has been fitted a first time over the distal end 4b of the external body 4.

The sampling or transfusion device of the invention incorporating protection means therefore conforms perfectly to hygiene and safety conditions imposed in the medical world, being very simple to use and employing the usual gestures employed in the medical environment. As a result there is no risk of injury to or of manipulation errors by medical personnel.

A perfect seal is obtained in the second embodiment of the invention. FIG. 11 shows more particularly that the protective cap 14 of the second embodiment includes a tubular cap 23 that is attached to the bottom of the protective cap 14, has an outside diameter D1 that is smaller than the inside diameter D2 of the protective tube 5 and is adapted to cover the projecting portion of the needle 3 upon abutting against the distal end 1b of the central body 1.

A seal is therefore provided in the vicinity of the distal end 1b of the central body 1 by virtue of an annular portion of the tubular cap 23 fitting over the central body 1. This prevents any liquid present in the tubular cap 23 escaping and contaminating the external environment.

In the second embodiment shown in FIG. 11, the tubular cap 23 is made from an elastomer material and the beveled end 32 of the needle 3 is embedded in the end wall 23a of the tubular cap 23, without passing through it, when the protective cap 14 is fitted over the distal end 4b of the external body 4. The sampling or transfusion device is therefore perfectly sealed.

As shown in FIG. 7, the beveled end 32 of the needle 3 is also embedded in the end wall 23a of the tubular cap 23 when the protective tube 5 is in the proximal retracted position and the sampling or transfusion device is on the point of being used. Hospital personnel have then already connected the transfusion line 2 to the proximal end 1a of the central body 1 and liquid from the transfusion sachet is filling the transfusion line 2 and the needle 3. The beveled end 32 of the needle 3 being embedded in the end wall 23a of the tubular cap 23, the liquid present in the needle 3 and in the transfusion sachet cannot flow out and contaminate the external environment. This greatly facilitates the work of hospital personnel by enabling them to connect a transfusion sachet via a transfusion line 2 with no risk of loss of transfusion liquid and with no risk of contaminating the environment.

The central body 1, the external body 4 and the protective cap 14 may advantageously be made of plastic material. Using this kind of material minimizes the weight of the sampling or transfusion device of the invention and means that it can be manufactured industrially, quickly and economically. Furthermore, its low weight contributes to its easy handling.

Figure 6:
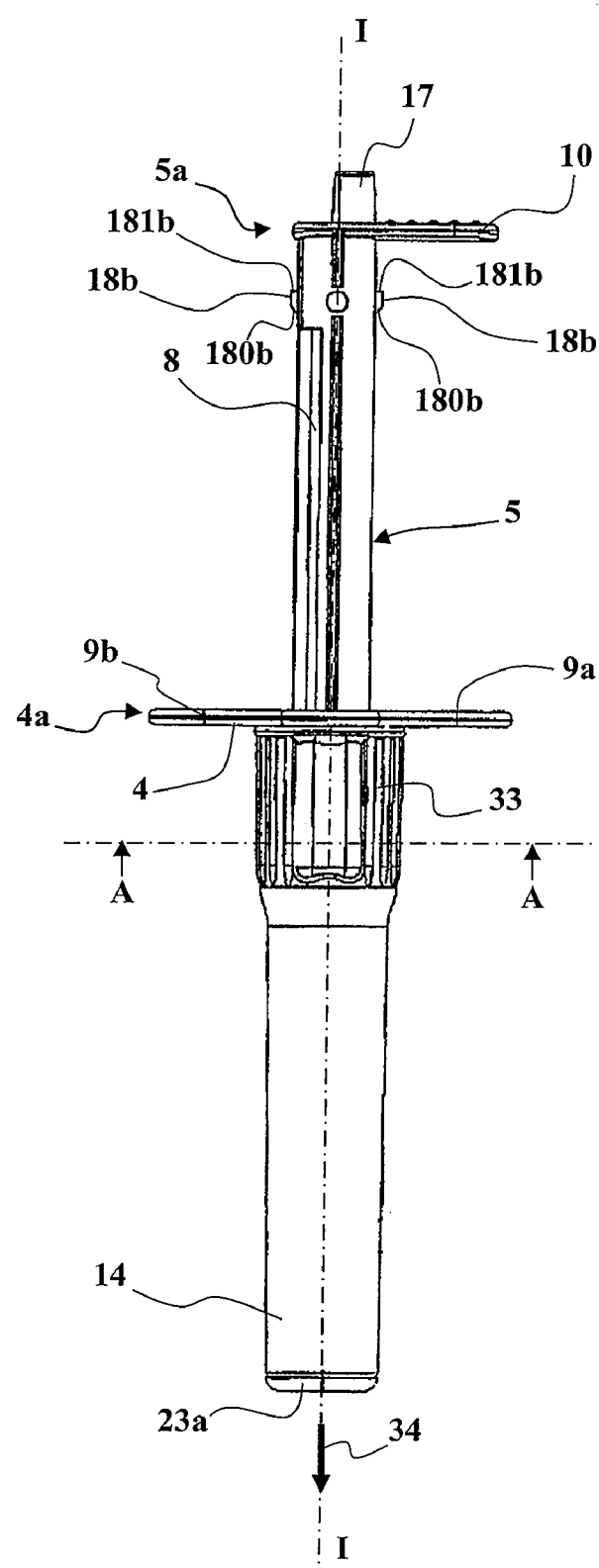
FIG. 6 is a front view of a second embodiment of a sampling or transfusion device with protection means.

In the second embodiment of the invention, as shown in FIG. 6 in particular, the protective tube 5 includes raised patterns 33 on its exterior surface. These raised patterns 33 facilitate holding of the protective cap 14 by the user in order to remove it in the direction indicated by the arrow 34.

The present invention is not limited to the embodiments that have been explicitly described and includes variations and generalizations thereof that fall within the scope of the following claims.

The invention claimed is:

1. Bodily fluid sampling or transfusion device incorporating protection means, said device including:
    a longitudinal hollow central body that enables a fluid to flow between a first end and a second end, is provided at its proximal end with means for connecting it to a sampling or transfusion line and is attached to a coaxial needle that projects from its distal end,
    means for selectively covering the projecting portion of the needle after use,
    a longitudinal hollow external body that has a peripheral tubular wall, is attached to the central body, is disposed concentrically around the central body and is conformed to constitute holding means for a user to hold onto,
    an annular passage between the central body and the external body,
    a protective tube that can slide longitudinally in the annular passage between the external body and the central body and has a proximal holding end for moving it selectively between, on one hand a proximal retracted position in which the needle is not covered by the protective tube or only very slightly covered thereby so that it can be used to draw a sample or to administer a transfusion, and on the other hand a distal protection position in which the protective tube covers the needle over its entire length,
    at least one radial fixing bridge attaching the external body to the central body and extending radially from the central body to the external body, and
    at least one longitudinal slot that extends over at least a portion of the length of the protective tube and in which said at least one radial fixing bridge slides during sliding movement of the protective tube relative to the central body and the external body, wherein:
    the central body, the radial fixing bridge and the external body are in one piece, and
    the longitudinal slot extends as far as the distal end of the protective tube.

2. Device according to claim 1, wherein the external body includes at least one radial holding tab extending radially away from the external body in the vicinity of its proximal end.

3. Device according to claim 1, wherein the proximal holding end of the protective tube includes at least one radial pusher tab extending radially away from at least a portion of the circumference of the protective tube.

4. Device according to claim 3, wherein:
    the proximal holding end of the protective tube includes a protuberance extending longitudinally along at least a portion of the protective tube beyond the radial pusher tab, and
    the protuberance extends from said at least a portion of the circumference of the protective tube from which the radial pusher tab extends radially.

5. Device according to claim 1, including means for locking the protective tube in the distal protection position and/or in the proximal retracted position.

6. Device according to claim 5, wherein the proximal retracted position locking means include:
    a first annular peripheral notch on the protective tube in the vicinity of its distal end, and
    at least one elastic radial locking lug extending radially from a distal end of the external body and engaging in the first annular peripheral notch when the protective tube is in the proximal retracted position.

7. Device according to claim 5, wherein the distal protection position locking means include:
- a second annular peripheral notch or a shoulder with a face facing toward the proximal holding end on the protective tube in the vicinity of its proximal holding end, and
- at least one elastic radial locking lug extending radially from the distal end of the external body and accommodated in the second annular peripheral notch or located over the shoulder when the protective tube is in the distal protection position.

8. Device according to claim 5, wherein the proximal retracted position locking means include:
- at least one first stop extending radially away from the protective tube in the vicinity of its distal end, and
- at least one longitudinal locking lug in an opening in the peripheral tubular wall of the external body that is adapted to be flexed elastically in the radial direction and has a free end oriented toward the proximal end of the external body adapted to abut against the first stop when the protective tube is in the proximal retracted position.

9. Device according to claim 8, wherein the distal protection position locking means include:
- at least one second stop extending radially away from the protective tube in the vicinity of its proximal end, and
- an opening in the locking lug adapted to receive the second stop when the protective tube is in the distal protection position.

10. Device according to claim 1, including a removable blind tubular protective cap that is conformed to fit over the distal end of the external body around the projecting portion of the needle and is of sufficient diameter to receive the projecting distal portion of the protective tube in the distal protection position.

11. Device according to claim 10, wherein, when fitted over the distal end of the external body, the blind tubular protective cap opposes elastic radial expansion of said at least one locking lug and thereby prevents sliding of the protective tube.

12. Device according to claim 10, wherein the blind tubular protective cap includes at its closed end retaining means for retaining the protective tube in the distal protection position.

13. Device according to claim 12, wherein the retaining means for retaining the protective tube are conformed to engage in a first annular peripheral notch of the protective tube when the protective tube is in the distal protection position and the protective cap is fitted over the distal end of the external body.

14. Device according to claim 10, wherein the protective cap has raised patterns on its exterior surface for holding it by.

15. Device according to claim 1, wherein the central body, the external body and the protective cap are of plastic material.

16. Device according to claim 10, wherein the protective cap includes a tubular cap that is attached to the closed end of the protective cap, has an exterior diameter less than the interior diameter of the protective tube and is adapted to cover the projecting portion of the needle upon abutting against the distal end of the central body.

17. Device according to claim 16, wherein the tubular cap is of elastomer and the needle is embedded in its closed end wall without passing through it when the protective cap is fitted over the distal end of the external body.

18. Device according to claim 1, wherein the protective tube includes at least one longitudinal rib adapted to cooperate with at least one longitudinal groove on the external body to guide the protective tube when it slides in the external body.

* * * * *